US011651189B2

(12) United States Patent
Kalkstein et al.

(10) Patent No.: US 11,651,189 B2
(45) Date of Patent: *May 16, 2023

(54) METHODS AND SYSTEMS OF EVALUATING A RISK OF A GASTROINTESTINAL CANCER (71) Applicant: Medial Research Ltd., Kfar-Malal (IL)

(72) Inventors: Nir Kalkstein, Herzlia (IL); Yaron Kinar, Tel-Aviv (IL); Varda Shalev, RaAnana (IL); Gabriel Chodick, Givataim (IL); Inbal Goldshtein, Ramat-HaSharon (IL)

(73) Assignee: Medial Research Ltd., Kfar Malal (IL)

( * ) Notice: Subject to any disclaimer, the term of this patent is extended or adjusted under 35 U.S.C. 154(b) by 757 days.

This patent is subject to a terminal disclaimer.

(21) Appl. No.: 16/658,087

(22) Filed: Oct. 20, 2019

(65) Prior Publication Data

US 2020/0050917 A1 Feb. 13, 2020

Related U.S. Application Data (60) Continuation of application No. 15/298,372, filed on Oct. 20, 2016, now Pat. No. 10,452,970, which is a division of application No. 14/347,245, filed as application No. PCT/IL2013/050368 on May 2, 2013, now Pat. No. 9,474,490.

(60) Provisional application No. 61/641,979, filed on May 3, 2012.

(51) Int. Cl.
G06N 3/02 (2006.01)
G01N 33/574 (2006.01)
G16H 50/20 (2018.01)
G16H 50/30 (2018.01)
A61B 5/00 (2006.01)

(52) U.S. Cl.
CPC .......... *G06N 3/02* (2013.01); *A61B 5/7275* (2013.01); *G01N 33/57419* (2013.01); *G01N 33/57446* (2013.01); *G16H 50/20* (2018.01); *G16H 50/30* (2018.01); *G01N 2800/50* (2013.01)

(58) Field of Classification Search
CPC .......... G06N 3/02; G16H 50/30; G16H 50/20; A61B 5/7275; G01N 33/57419; G01N 33/57446
See application file for complete search history.

(56) References Cited

U.S. PATENT DOCUMENTS

| 5,692,220 | A  | 11/1997 | Diamond et al. |
| 6,059,724 | A  | 5/2000  | Campbell et al. |
| 8,512,240 | B1 | 8/2013  | Zuckerman-Stark et al. |
| 2002/0025543 | A1 | 2/2002 | Serrero |
| 2004/0122703 | A1 | 6/2004 | Walker et al. |
| 2006/0173717 | A1 | 8/2006 | Scheuner |
| 2009/0069639 | A1 | 3/2009 | Linssen et al. |
| 2009/0150315 | A1 | 6/2009 | Wirtz et al. |
| 2010/0009401 | A1 | 1/2010 | Imaizumi et al. |
| 2010/0076787 | A1 | 3/2010 | Naylor et al. |
| 2010/0184046 | A1 | 7/2010 | Klass et al. |
| 2012/0070853 | A1 | 3/2012 | Johansen et al. |
| 2014/0235956 | A1 | 8/2014 | Kalkstein et al. |
| 2017/0039334 | A1 | 2/2017 | Kalkstein et al. |

FOREIGN PATENT DOCUMENTS

| CN | 1268033 | 9/2000 |
| CN | 1681607 | 10/2005 |
| CN | 1682111 | 10/2005 |
| JP | 2001-511680 | 8/2001 |
| WO | WO 98/35609 | 8/1998 |
| WO | WO 2004/020112 | 3/2004 |
| WO | WO 2006/102526 | 9/2006 |
| WO | WO 2010/048282 | 4/2010 |
| WO | WO 2011/060098 | 5/2011 |
| WO | WO 2011/063389 | 5/2011 |
| WO | WO 2013/164823 | 11/2013 |

OTHER PUBLICATIONS

Requisition by the Examiner dated May 5, 2020 From the Innovation, Science and Economic Development Canada, Canadian Intellectual Property Office Re. Application No. 2,865,892. (11 Pages).
Examination Report Under Sections 12 & 13 of the Patents Act, 1970 and the Patents Rules, 2003 dated Jul. 10, 2020 From the Government of India, Intellectual Property India, Patents, Designs, Trade Marks, Geographical Indications, The Patent Office Re. Application No. 1809/MUMNP/2014. (9 Pages).
Ludwig et al. "Biomarkers in Cancer Staging, Prognosis and Treatment Selection", Nature Reviews Cancer, 5(11): 845-854, Published Online Oct. 20, 2005.
Notice of Patent Grant dated Dec. 26, 2019 From the Korean Intellectual Property Office Re. Application No. 10-2014-7026479 and Its Translation Into English. (9 Pages).

(Continued)

*Primary Examiner* — Jerry Lin (57) ABSTRACT

A method of evaluating gastrointestinal cancer risk. The method comprises generating a set of features comprising a plurality of current blood test results from a blood collected from a target individual, providing at least one classifier generated according to an analysis of a plurality of respective historical blood test results of each of another of a plurality of sampled individuals, and evaluating, using a processor, a gastrointestinal cancer risk of the target individual by classifying the set of features using the at least one classifier.

15 Claims, 10 Drawing Sheets

(56) References Cited

OTHER PUBLICATIONS

Communication Pursuant to Article 94(3) EPC dated Jun. 23, 2016 From the European Patent Office Re. Application No. 13784595.4.
Examination Report dated Nov. 22, 2016 From the Instituto Mexicano de la Propiedad Industrial, IMPI Re. Application No. MX/a/2014/011202 and Its Translation Into English. (4 Pages).
Grounds of Reasons of Rejection dated Jun. 18, 2019 From the Korean Intellectual Property Office Re. Application No. 10-2014-7026479 and Its Summary in English.
International Preliminary Report on Patentability dated Nov. 13, 2014 From the International Bureau of WIPO Re. Application No. PCT/IL2013/050368.
International Search Report and the Written Opinion dated Aug. 8, 2013 From the International Searching Authority Re. Application No. PCT/IL2013/050368.
Notice Of Allowance dated Jun. 14, 2016 From the Re. U.S. Appl. No. 14/347,245.
Notice of Reason for Rejection dated Apr. 7, 2017 From the Japan Patent Office Re. Application No. 2015-509566 and Its Translation Into English. (5 Pages).
Notification of Office Action dated May 4, 2016 From The State Intellectual Property Office of the People's Republic of China Re. Application No. 201380022626.6.
Notification of Office Action dated Sep. 22, 2015 From The State Intellectual Property Office of the People's Republic of China Re. Application No. 201380022626.6 and Its Translation Into English.
Notification of Office Action dated Jul. 29, 2016 From The State Intellectual Property Office of the People's Republic of China Re. Application No. 201380022626.6 and Its Translation Into English.
Notification of Office Action dated Nov. 29, 2016 From The State Intellectual Property Office of the People's Republic of China Re. Application No. 201380022626.6 and Its Translation Into English. (7 Pages).
Office Action dated Feb. 16, 2015 From the Israel Patent Office Re. Application No. 233900.
Official Action dated Nov. 2, 2018 From the Re. U.S. Appl. No. 15/298,372. (16 pages).
Official Action dated Dec. 3, 2014 From the Re. U.S. Appl. No. 14/347,245.
Official Action dated Nov. 16, 2015 From the Re. U.S. Appl. No. 14/347,245.
Patent Examination Report dated Oct. 17, 2016 From the Australian Government, IP Australia Re. Application No. 2013255401.
Request for Examination and Search Report dated Apr. 7, 2017 From the ROSPATENT, Federal Government Insitution, Federal Institute of Industrial Property of the Federal Service for Intellectual Peroperty, Patents and Trademarks of the Russian Federation Re. Application No. 2014140114 and Its Translation of Office Action Into English. (13 Pages).
Requisition by the Examiner dated Jun. 14, 2019 From the Innovation, Science and Economic Development Canada, Canadian Intellectual Property Office Re. Application No. 2,865,892. (4 Pages).
Restriction Official Action dated Aug. 7, 2015 From the Re. U.S. Appl. No. 14/347,245.
Supplementary European Search Report and the European Search Opinion dated Oct. 19, 2015 From the European Patent Office Re. Application No. 13784595.4.
Translation Dated Mar. 1, 2015 of Office Action dated Feb. 16, 2015 From the Israel Patent Office Re. Application No. 233900.
Translation Dated Jul. 7, 2019 of Grounds of Reasons of Rejection dated Jun. 18, 2019 From the Korean Intellectual Property Office Re. Application No. 10-2014-7026479. (1 Page).
Translation of Notification of Office Action dated May 4, 2016 From The State Intellectual Property Office of the People's Republic of China Re. Application No. 201380022626.6.
Ballinger "Gastroenterology and Anemia", Medicine, 35(3): 142-146, 2006.
Chua et al. "Neutrophil/Lymphocyte Ratio Predicts Chemotherapy Outcomes in Patients With Advanced Colorectal Cancer", British Journal of Cancer, XP055218049, 104(8): 1288-1295, Published Online Mar. 29, 2011. Abstract.
George-Gay et al. "Understanding the Complete Blood Count With Differential", Journal of PeriAnesthesia Nursing, 18(2): 96-117, Apr. 2003.
Koulaouzidis et al. "Hemoglobin and Red Cell Indices as Predictors of Gastrointestinal Malignancy", American Journal of Gastroenterology, XP008177675, 101(Suppl.S2): S134, #272, Sep. 2006. Abstract.
Mahadavan et al. "Exfoliated Colonocyte DNA Levels and Clinical Features in the Diagnosis of Colorectal Cancer: A Cohort Study in Patients Referred for Investigation", Colorectal Disease, XP055218047, 14(3): 306-313, Feb. 7, 2012. Abstract.
Spell et al. "The Value of A Complete Blood Count In Predicting Cancer of the Colon", Cancer Detection and Prevention, 28(1): 37-42, 2004.
Search Report and Technical Report dated Jan. 29, 2020 From the Servico Publico Federal, Ministerio da Economia, Institute National da Propriedade Industrial do Brasil Re. Application No. BR112014 022991-0 and Its Translation Into English. (8 Pages).

| Recall (%) | Lift | Est. Precision (%) | Specificity (%) |
|---|---|---|---|
| 5 | 38 ± 1 | 24.9 ± 0.7 | 99.930 ± 0.004 |
| 10 | 31 ± 1 | 20.1 ± 0.7 | 99.79 ± 0.01 |
| 20 | 19.0 ± 0.5 | 12.2 ± 0.3 | 99.16 ± 0.03 |
| 50 | 6.0 ± 0.1 | 3.90 ± 0.05 | 92.9 ± 0.1 |
| 70 | 3.70 ± 0.05 | 2.40 ± 0.03 | 81.6 ± 0.2 |

FIG. 4A

| Recall (%) | Lift | Est. Precision (%) | Specificity (%) |
|---|---|---|---|
| 5 | 43 ± 2 | 27.5 ± 1.5 | 99.940 ± 0.007 |
| 10 | 33 ± 2 | 21.5 ± 1.0 | 99.81 ± 0.02 |
| 20 | 19.6 ± 0.5 | 12.70 ± 0.15 | 99.21 ± 0.01 |
| 50 | 5.5 ± 0.2 | 3.60 ± 0.15 | 91.3 ± 0.4 |
| 70 | 3.27 ± 0.08 | 2.10 ± 0.05 | 79.2 ± 0.5 |

FIG. 4B

| Recall (%) | Lift | Est. Precision (%) | Specificity (%) |
|---|---|---|---|
| 5 | 50.5 ± 1.5 | 32.5 ± 1 | 99.960 ± 0.003 |
| 10 | 41.5 ± 1.5 | 27 ± 1 | 99.87 ± 0.01 |
| 20 | 23.6 ± 0.5 | 15.4 ± 0.3 | 99.38 ± 0.02 |
| 50 | 7.0 ± 0.2 | 4.5 ± 0.1 | 93.3 ± 0.2 |
| 70 | 3.66 ± 0.06 | 2.40 ± 0.05 | 81.5 ± 0.3 |

FIG. 4C

| Feature | Importance |
|---|---|
| Age | 206.06278 |
| Hemoglobin Current | 97.94094 |
| Hematocrit Current | 75.68337 |
| MCHC-M Current | 65.28961 |
| MCH 3yrs history | 61.24915 |
| RDW Current | 59.87631 |
| MCH 1.5yrs history | 59.41473 |
| Hemoglobin 3yrs history | 47.9564 |
| RBC Current | 42.17517 |
| MCH Current | 41.98025 |
| Hemoglobin 1.5yrs history | 41.33024 |
| Platelets Current | 39.70198 |
| Hematocrit 3yrs history | 39.57657 |
| Neutrophils% Current | 34.09554 |
| MCV 1.5yrs history | 33.75738 |
| Hematocrit 1.5yrs history | 32.66408 |
| MCV 3yrs history | 32.25354 |
| RDW 1.5yrs history | 31.58052 |
| Neutrophils# Current | 31.49156 |
| RDW 3yrs history | 31.433 |
| Eosinophils% Current | 29.21783 |
| Monocytes# Current | 29.07631 |
| MPV Current | 29.039 |
| Monocytes% Current | 28.70935 |
| WBC Current | 27.77065 |
| MCV Current | 27.16896 |
| Eosinophils# Current | 26.03917 |
| Platelets 3yrs history | 25.98912 |
| Platelets 1.5yrs history | 24.74618 |
| MCHC-M 3yrs history | 23.69543 |
| MCHC-M 1.5yrs history | 22.48561 |
| MPV 3yrs history | 21.91487 |
| RBC 3yrs history | 21.77685 |
| 500 days cbc count | 21.66158 |
| RBC 1.5yrs history | 20.76823 |
| MPV 1.5yrs history | 20.40031 |
| Neutrophils% 1.5yrs history | 20.29873 |
| Neutrophils% 3yrs history | 19.53775 |
| Eosinophils% 3yrs history | 19.23888 |
| Monocytes% 3yrs history | 19.03372 |
| Eosinophils% 1.5yrs history | 18.81205 |
| Monocytes% 1.5yrs history | 18.41941 |
| Neutrophils# 1.5yrs history | 18.38092 |
| Basophils% 3yrs history | 18.17924 |
| Neutrophils# 3yrs history | 18.08296 |
| Basophils% 1.5yrs history | 17.88699 |
| WBC 3yrs history | 17.87557 |
| Basophils% Current | 17.7247 |
| Monocytes# 3yrs history | 17.72236 |
| Eosinophils# 3yrs history | 17.70108 |
| 1500 days cbc count | 17.62082 |
| WBC 1.5yrs history | 17.4697 |
| Monocytes# 1.5yrs history | 17.35154 |
| Eosinophils# 1.5yrs history | 17.14117 |
| Basophils# Current | 14.47268 |
| 1000 days cbc count | 13.73909 |
| Basophils# 1.5yrs history | 12.74062 |
| Basophils# 3yrs history | 12.58885 |

FIG. 5A

| feaure1 | feture2 | Correlation | auc feature1 | auc feature2 | auc both |
|---|---|---|---|---|---|
| [Hemoglobin] | [Hematocrit] | 0.938058 | 0.7416 | 0.719 | 0.7411 |
| [Neutrophils] | [Lymphocytes] | -0.930858 | 0.5424 | 0.5737 | 0.59 |
| [MCV] | [MCH] | 0.873668 | 0.5915 | 0.6453 | 0.689 |
| [RBC] | [Hematocrit] | 0.774977 | 0.6582 | 0.719 | 0.7249 |
| [RBC] | [Hemoglobin] | 0.724278 | 0.6582 | 0.7416 | 0.7461 |
| [RBC] | [MCV] | -0.534006 | 0.6582 | 0.5915 | 0.725 |

FIG. 5B

| Period (Days) | 5% Sens. Lift | 5% Sens. Spec. | 10% Sens. Lift | 10% Sens. Spec. | 20% Sens. Lift | 20% Sens. Spec. | 50% Sens. Lift | 50% Sens. Spec | 70% Sens. Lift | 70% Sens. Spec |
|---|---|---|---|---|---|---|---|---|---|---|
| 30-90 | 99 | 99.98 | 87 | 99.95 | 48 | 99.71 | 12 | 96.23 | 5.6 | 87.90 |
| 90-180 | 65 | 99.95 | 53 | 99.86 | 32 | 98.97 | 8.3 | 93.77 | 4.6 | 84.87 |
| 180-360 | 26 | 99.84 | 23 | 99.64 | 14 | 98.68 | 5.6 | 91.27 | 3.5 | 80.47 |
| 360-540 | 18 | 99.75 | 13 | 99.23 | 8 | 97.62 | 4.5 | 89.06 | 3.2 | 78.31 |
| 540-720 | 10 | 99.54 | 8.6 | 98.89 | 6.1 | 96.76 | 3.9 | 87.28 | 3.1 | 77.31 |

FIG. 6

| Recall (%) | Lift | Est. Precision (%) | Specificity (%) |
|---|---|---|---|
| 5 | 58.0 ± 3.5 | 27 ± 2 | 99.950 ± 0.004 |
| 10 | 44.5 ± 1.5 | 20.5 ± 0.8 | 99.850 ± 0.008 |
| 20 | 28.3 ± 0.7 | 13.0 ± 0.3 | 99.44 ± 0.02 |
| 50 | 7.6 ± 0.2 | 3.5 ± 0.1 | 93.8 ± 0.2 |
| 70 | 3.52 ± 0.06 | 1.6 ± 0.03 | 80.5 ± 0.4 |

| Thin results | | |
|---|---|---|
| Sens at 90% | AUC | Colon |
| 55.80% | 0.85 | 90-540/40-100: |
| 48.00% | 0.79 | 90-540/50-75: |
| 67.90% | 0.89 | 30-270/40-100: |
| 60.20% | 0.84 | 30-270/50-75: |
| 40.90% | 0.8 | 360-720/40-100: |
| 30.90% | 0.73 | 360-720/50-75: |
| Sens at 90% | AUC | Stomach |
| 48.30% | 0.83 | 90-540/40-100: |
| 41.90% | 0.76 | 90-540/50-75: |
| 61.80% | 0.87 | 30-270/40-100: |
| 56.70% | 0.8 | 30-270/50-75: |
| 36.40% | 0.79 | 360-720/40-100: |
| 27.50% | 0.71 | 360-720/50-75: |
| Sens at 90% | AUC | Rectum |
| 40.50% | 0.79 | 90-540/40-100: |
| 31.30% | 0.72 | 90-540/50-75: |
| 48.40% | 0.81 | 30-270/40-100: |
| 40.00% | 0.74 | 30-270/50-75: |
| 32.90% | 0.78 | 360-720/40-100: |
| 28.40% | 0.73 | 360-720/50-75: |
| Sens at 90% | AUC | Oesophagus |
| 37.80% | 0.79 | 90-540/40-100: |
| 31.40% | 0.74 | 90-540/50-75: |
| 45.00% | 0.81 | 30-270/40-100: |
| 41.30% | 0.76 | 30-270/50-75: |
| 34.00% | 0.79 | 360-720/40-100: |
| 24.30% | 0.72 | 360-720/50-75: |

FIG. 9

MEN-ANEMIA RESULTS

| age | Hgb |
|---|---|
| 20-59 | 13.7 |
| >=60 | 13.2 |

| | | | anemia | no anemia | | sens | spec |
|---|---|---|---|---|---|---|---|
| time windo | 90-365 | cancer-pos | 256 | 328 | | 0.44 | 0.86 |
| age | 40-100 | cancer_neg | 29,651 | 181,670 | | | |
| | | prob | 0.86% | 0.18% | | | |

| | | | anemia | no anemia | | sens | spec |
|---|---|---|---|---|---|---|---|
| time windo | 30-720 | cancer-pos | 389 | 400 | | 0.49 | 0.86 |
| age | 40-100 | cancer_neg | 30,172 | 181,541 | | | |
| | | prob | 1.27% | 0.22% | | | |

| | | | anemia | no anemia | | sens | spec |
|---|---|---|---|---|---|---|---|
| time windo | 365-720 | cancer-pos | 157 | 365 | | 0.30 | 0.87 |
| age | 40-100 | cancer_neg | 28,289 | 181,326 | | | |
| | | prob | 0.55% | 0.20% | | | |

| | | | anemia | no anemia | | sens | spec |
|---|---|---|---|---|---|---|---|
| time windo | 30-720 | cancer-pos | 231 | 307 | | 0.43 | 0.87 |
| age | 50-75 | cancer_neg | 15,186 | 100,178 | | | |
| | | prob | 1.50% | 0.31% | | | |

| | | | anemia | no anemia | | sens | spec |
|---|---|---|---|---|---|---|---|
| time windo | 365-720 | cancer-pos | 91 | 280 | | 0.25 | 0.87 |
| age | 50-75 | cancer_neg | 14,467 | 100,079 | | | |
| | | prob | 0.63% | 0.28% | | | |

FIG. 10

METHODS AND SYSTEMS OF EVALUATING A RISK OF A GASTROINTESTINAL CANCER

RELATED APPLICATIONS

This application is a continuation of U.S. patent application Ser. No. 15/298,372 filed on Oct. 20, 2016, which is a division of U.S. patent application Ser. No. 14/347,245 filed on Mar. 26, 2014, now U.S. Pat. No. 9,474,490, which is a National Phase of PCT Patent Application No. PCT/IL2013/050368 having International Filing Date of May 2, 2013, which claims the benefit of priority under 35 USC § 119(e) of U.S. Provisional Patent Application No. 61/641,979 filed on May 3, 2012. The contents of the above applications are all incorporated by reference as if fully set forth herein in their entirety.

FIELD AND BACKGROUND OF THE INVENTION

The present invention, in some embodiments thereof, relates to cancer diagnosis and, more particularly, but not exclusively, to methods and systems of evaluating a risk of cancer.

A diagnosis of colorectal cancer includes diagnosis based on the immunological fecal occult blood reaction, diagnosis by colonoscopy, and the like. However, diagnosis based on a fecal occult blood test does not serve as definitive diagnosis, and most of the persons with positive-finding are false-positive. Furthermore, in regard to early colorectal cancer, there is a concern that both the detection sensitivity and the detection specificity become lower in the diagnosis based on a fecal occult blood test or the diagnosis by colonoscopy. In particular, early cancer in the right side colon is frequently overlooked when diagnosed by a fecal occult blood test. Diagnostic imaging by CT (computer tomography), MRI (magnetic resonance imaging), PET (positron emission computerized-tomography) or the like is not suitable for the diagnosis of colorectal cancer.

On the other hand, colorectal biopsy by colonoscopy serves as definitive diagnosis, but is a highly invasive examination, and implementing colonoscopic examination at the screening stage is not practical. Furthermore, invasive diagnosis such as colonoscopy gives a burden to individuals such as accompanying pain, and there may also be a risk of bleeding upon examination, or the like.

During the last years, some new methods have been developed for diagnosis of colorectal cancer. For example, U.S. Patent Application Publication No. 2010/0009401 describes a method of evaluating colorectal cancer, where amino acid concentration data on the concentration value of amino acid in blood collected from a subject to be evaluated is measured, and a colorectal cancer state in the subject is evaluated based on the concentration value of at least one of Arg, Cys, Om, Trp, Glu, ABA, Val, Phe, Leu, Gln, Ile and His contained in the measured amino acid concentration data of the subject.

SUMMARY OF THE INVENTION

According to some embodiments of the present invention, there are provided a computerized method of evaluating gastrointestinal cancer risk. The method comprises generating a set of features comprising a plurality of current blood test results from a blood collected from a target individual, providing at least one classifier generated according to an analysis of a plurality of respective historical blood test results of each of another of a plurality of sampled individuals; and evaluating, using a processor, a gastrointestinal cancer risk of the target individual by classifying the set of features using the at least one classifier. Each of the plurality of historical and current blood test results comprises results of at least one the following blood tests: red blood cells (RBC), hemoglobin (HGB), and hematocrit (HCT) and at least one result of the following blood tests hemoglobin (MCH) and mean corpuscular hemoglobin concentration (MCHC). Optionally, the blood test results are extracted from a complete blood count (CBC) test.

Optionally, the set of features comprises an age of the target individual; wherein the at least one classifier is generated according to an analysis of the age of each of another of a plurality of sampled individuals.

Optionally, each of the plurality of historical and current blood test results comprises results of red cell distribution width (RDW).

Optionally, each of the plurality of historical and current blood test results comprises results of Platelets hematocrit (PCT).

Optionally, each of the plurality of historical and current blood test results comprises results of mean cell volume (MCV).

Optionally, each of the plurality of historical and current blood test results comprises at least one of the following blood tests: white blood cell count—WBC (CBC); mean platelet volume (MPV); mean cell; platelet count (CBC); eosinophils count; neutrophils percentage; monocytes percentage; eosinophils percentage; basophils percentage; and neutrophils count; monocytes count.

Optionally, the at least one classifier comprises a member of a group consisting of: a weighted linear regression classifier, a K-Nearest neighbors (KNN) classifier, and a random forest classifier.

Optionally, the set of features comprises at least one demographic characteristic of the target individual and the at least one classifier generated according to an analysis of respective the at least one demographic characteristic of each of the plurality of sampled individuals.

Optionally, the method further comprises selecting the at least one classifier according to at least one demographic characteristic of the individual from a plurality of classifiers each generated according to a plurality of respective historical blood test results of sampled individuals having at least one different demographic characteristic.

Optionally, the plurality of blood test results comprises at least one result from the following plurality of blood tests: biochemical blood test results may include any of the following blood test results Albumin, Calcium, Chloride, Cholesterol, Creatinine, high density lipoprotein (HDL), low density lipoprotein (LDL), Potassium, Sodium, Triglycerides, Urea, and/or Uric Acid.

According to some embodiments of the present invention, there are provided a gastrointestinal cancer evaluating system. The system comprises a processor, a memory unit which stores at least one classifier generated according to an analysis of a plurality of historical blood test results of each of another of a plurality of sampled individuals, and an input unit which receives a plurality of current blood test results taken from a blood of a target individual, and a gastrointestinal cancer evaluating module which evaluates, using the processor, a gastrointestinal cancer risk of the target individual by classifying, using the at least one classifier, a set of features extracted from the plurality of current blood test results. The plurality of historical and current blood test results comprises results of at least one the following of plurality of blood tests: red blood cells (RBC), hemoglobin (HGB), and hematocrit (HCT) and at least one result of the following blood tests hemoglobin (MCH) and mean corpuscular hemoglobin concentration (MCHC).

Optionally, each of the plurality of historical and current blood test results comprises results of red cell distribution width (RDW).

Optionally, each of the plurality of historical and current blood test results comprises results of Platelets hematocrit (PCT).

Optionally, each of the plurality of historical and current blood test results comprises of mean cell volume (MCV).

According to some embodiments of the present invention, there are provided a method of generating a classifier for a CRC risk evaluation. The method comprises providing a plurality of historical blood test results of each of another of a plurality of sampled individuals, generating a dataset having a plurality of sets of features each set generated according to respective plurality of historical blood test results of another the plurality of sampled individuals, generating at least one classifier according to an analysis the dataset, and outputting the at least one classifier.

Optionally, the generating comprises calculating and adding at least one manipulated version of an historical blood test result taken from a respective the plurality of historical blood test results as a feature to respective the set of features.

Optionally, the generating comprises weighting each the set of features according to a date of the respective plurality of historical blood test results.

Optionally, the generating comprises filtering the plurality of sets of features to remove outliers according to a standard deviation maximum threshold.

Optionally, the plurality of sets of features are weighted according to a date of the respective plurality of historical blood test results.

Optionally, the plurality of blood test results of at least one the following blood tests: red blood cells (RBC), hemoglobin (HGB), and hematocrit (HCT) and at least one result of the following blood tests hemoglobin (MCH) and mean corpuscular hemoglobin concentration (MCHC).

Optionally, each of the plurality of historical and current blood test results comprises results of red cell distribution width (RDW).

Optionally, each of the plurality of historical and current blood test results comprises results of Platelets hematocrit (PCT).

Optionally, each of the plurality of historical and current blood test results comprises results of mean cell volume (MCV).

More optionally, the method further comprises adding at least one demographic parameter of each of the plurality of sampled individuals to a respective the set of features.

More optionally, the at least one demographic parameter is a member of a group consisting of gender, age, residential zone, race and socio-economic characteristic.

More optionally, the generating comprises calculating and adding at least one manipulated version of the at least one demographic parameter as a feature to respective the set of features.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5A is an image of a table of an expended set of features which are listed according to their importance in a random forest classifier for men;

DESCRIPTION OF SPECIFIC EMBODIMENTS OF THE INVENTION

The present invention, in some embodiments thereof, relates to cancer diagnosis and, more particularly, but not exclusively, to methods and systems of evaluating a risk of cancer.

According to some embodiments of the present invention, there are provided methods and systems of evaluating gastrointestinal cancer risk by classifying a set of current blood test results of a target individual using one or more classifiers which are generated according to an analysis of historical blood test results of a plurality of individuals. The set of current blood test results includes at least one result of the following blood tests hemoglobin (HGB), hematocrit (HCT), and red blood cells (RBC) and at least one result of the following blood tests mean cell hemoglobin (MCH) and mean corpuscular hemoglobin concentration (MCHC) and the age of the target individual. Optionally, the set of current blood test results further includes one or more of the following blood tests: white blood cell count—WBC (CBC); mean platelet volume (MPV); mean cell volume (MCV); red cell distribution width (RDW); platelet count (CBC); eosinophils count; neutrophils percentage; monocytes percentage; eosinophils percentage; basophils percentage; neutrophils count; monocytes count; and Platelets hematocrit (PCT).

Optionally, the gastrointestinal cancer risk is evaluated by classifying biochemical blood test results of the target individual. In such embodiments, the classifiers are generated according to an analysis of historical biochemical blood test results of the plurality of individuals. The biochemical blood test results may include results of any of the following blood tests: Albumin, Calcium, Chloride, Cholesterol, Creatinine, high density lipoprotein (HDL), low density lipoprotein (LDL), Potassium, Sodium, Triglycerides, Urea, and/or Uric Acid.

Optionally, the gastrointestinal cancer risk is evaluated by classifying demographic characteristics of the target individual. In such embodiments, the classifiers are generated according to an analysis of demographic characteristics of the plurality of individuals.

Optionally, both the current blood test results of the target individual and the historical blood test results of sampled individuals are used for generating expended sets of features which include manipulated and/or weighted values. Optionally, each expended set of features is based on the demographic characteristics of a respective individual, for example as described below.

Optionally, the one or more classifiers are adapted to one or more demographic characteristics of the target individual. Optionally, the classifiers are selected to match one or more demographic characteristics of the target individual. In such embodiments, different classifiers may be used for women and men.

According to some embodiments of the present invention, there are provided methods and systems of generating one or more classifiers for gastrointestinal risk evaluation. The methods and systems are based on analysis of a plurality of historical blood test results of each of another of a plurality of sampled individuals and generating accordingly a dataset having a plurality of sets of features each generated according to respective historical blood test results. The dataset is then used to generate and output one or more classifiers, such as K-Nearest neighbors (KNN) classifiers, random forest classifiers, and weighted linear regression classifiers. The classifiers may be provided as modules for execution on client terminals or used as an online service for evaluating gastrointestinal cancer risk of target individuals based on their current blood test results.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
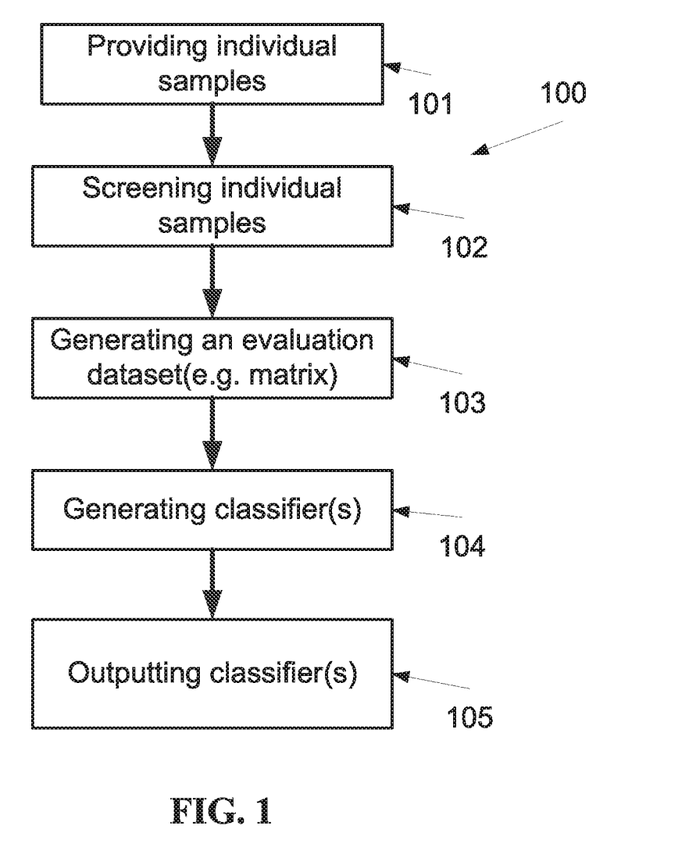
FIG. 1 is a flowchart of a method of generating one or more classifiers for estimating a gastrointestinal cancer risk score according to an analysis of a plurality of individual records, according to some embodiments of the present invention.
Figure 2:
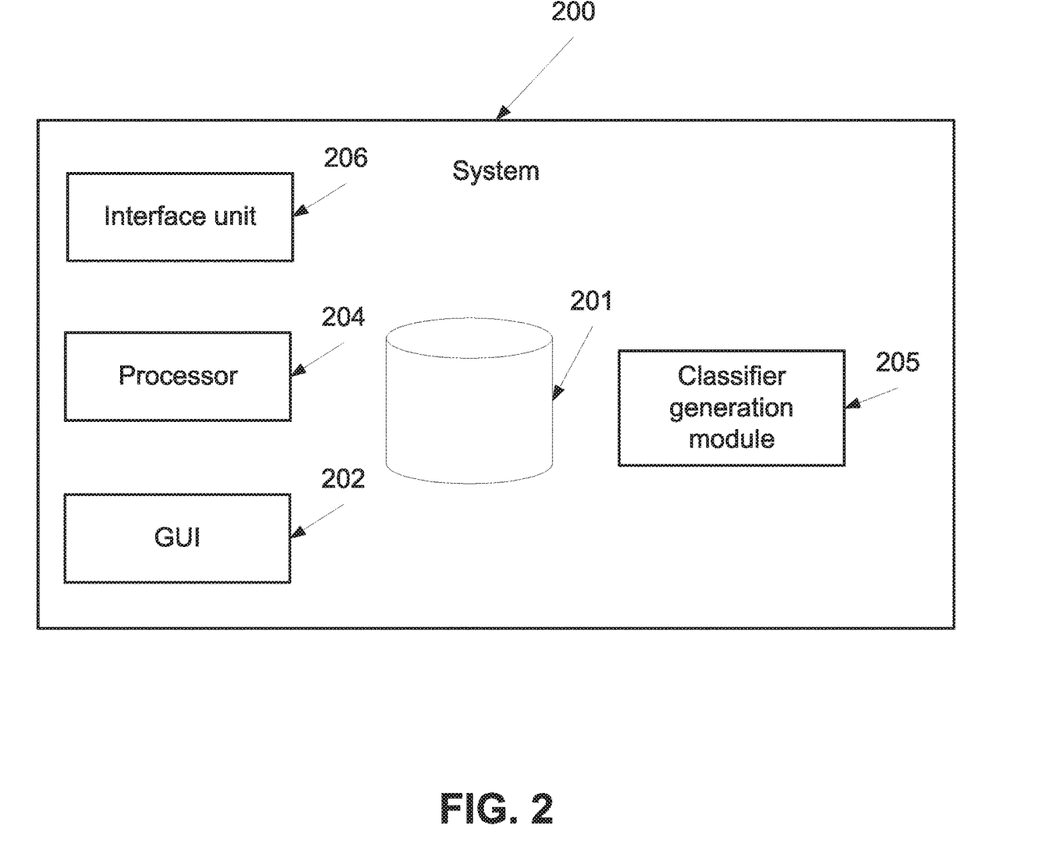
FIG. 2 is a schematic illustration of a system for generating one or more classifiers, for example by implementing the method depicted in FIG. 1, according to some embodiments of the present invention.

Reference is now made to FIG. 1, which is a flowchart of a method 100 of generating one or more classifiers for estimating a gastrointestinal cancer risk score according to an analysis of a plurality of historical test results of each of a plurality of diagnosed individuals, according to some embodiments of the present invention. As used herein, a gastrointestinal cancer may be colon, stomach, rectum, or esophagus cancer. Reference is also made to FIG. 2, which is a schematic illustration of a system 200 for generating classifier(s) for estimating gastrointestinal cancer risk scores, for example by implementing the method depicted in FIG. 1, according to some embodiments of the present invention.

The system 200 includes to one or more medical record database(s) 201 and/or connected to a medical record database interface. The database(s) 201 include a plurality of individual records, also referred to as a plurality of individual samples, which describe, for each of another of a plurality of sampled individuals, one or more sets of a plurality of historical test results each set of another individual, and optionally one or more demographic parameter(s) and a gastrointestinal cancer prognosis. The set of a plurality of historical test results, demographic parameter(s), such as age, and/or gastrointestinal cancer prognosis may be stored in a common sample record and/or gathered from a number of independent and/or connected databases. Optionally, the gastrointestinal cancer prognosis is a binary indication set according to a cancer registry record. The different test results may be of commonly performed blood tests and/or blood tests held during the same period. Optionally, some sets of a plurality of historical test results have missing blood test results. These results are optionally completed by weighted averaging of the available blood test results of other individuals. The method further includes a processor 204, a classifier generation module 205, and an interface unit 206, such as a network interface.

As used herein, a demographic parameter includes age, gender, race, weight, national origin, geographical region of residence and/or the like.

First, as shown at 101, one or more dataset(s) of a plurality of individual samples are provided.

Optionally, as shown at 102, the plurality of individual samples are screened and/or selected according to matching criteria. For example, the sample records are of individuals in the age of 40 or older who either appear in a cancer registry with colon cancer, and optionally without other types of cancer, or do not appear in the not appear there at the cancer registry. Optionally, sample records of individuals that appear in the cancer registry are taken only if the latest set of a plurality of historical test results they document was taken during a certain period before the registration of a respective individual in the cancer registry, for example during a period of at least 30 days before a current date and at most 2 years. Optionally, sample records of individuals that do not appear in the cancer registry are taken only if they include a set of a plurality of historical test results that creates an equal time-distribution (blood tests timing) for the positive and negative gastrointestinal cancer populations. The process of equating the time-distribution of the positive and negative samples also leads to omit at least some negative (non-registered) samples and to a change in the gastrointestinal prevalence in the data set.

Now, as shown at 103, an evaluation dataset, such as a matrix, is generated according to the sample data extracted from the sample records, for example by the classifier generation module 205. The evaluation dataset includes a plurality of sets of features, optionally expended. Each set of features is generated from each one of the screened and/or selected sample records. The set of features are optionally unprocessed features which includes actual blood test and/or demographic characteristic values.

As described above, each sample record includes one or more sets of a plurality of historical test results of a individual, each includes a combination blood test results, for example a combination of more than 10, 15, 20 and/or any intermediate number of blood test results. In one example, each extracted set of unprocessed features includes at least the following 18 blood test results: red blood cells (RBC); white blood cell count—WBC (CBC); mean platelet volume (MPV); hemoglobin (HGB); hematocrit (HCT); mean cell volume (MCV); mean cell hemoglobin (MCH); mean corpuscular hemoglobin concentration (MCHC); red cell distribution width (RDW); platelet count (CBC); eosinophils count; neutrophils percentage; monocytes percentage; eosinophils percentage; basophils percentage; neutrophils count; monocytes count; and Platelets hematocrit (PCT). In another example, each extracted set of unprocessed features includes at least result of the following blood tests HGB, HCT, and RBC, at least one result of the following blood tests MCH and MCHC and additional data reflecting the age of the target individual. Optionally, this extracted set of unprocessed features further includes one or more of the following blood tests RDW, Platelets, and MCV. Additionally, this extracted set of unprocessed features may further includes one or more of the following blood tests WBC, eosinophils count, neutrophils percentage and/or count, basophils percentage and/or count, and monocytes percentage and/or count.

Optionally, the set of unprocessed features is expended. The expended set of features contains features as the above unprocessed blood test results and/or one or more demographic parameter(s) and optionally manipulated blood test results and/or combination of blood test results, for instance as described below. For example, each feature in the set of expended features is based on a blood test result, a demographic characteristic, a combination of blood test result(s) and/or demographic characteristic(s), and/or a manipulation of blood test result(s) and/or demographic characteristic(s).

For example, when the set of unprocessed features includes 18 test results, an expended set of 114 features is generated based on the following:

1. 18 features, each includes another of the 18 blood test results.
2. 18 features, each includes a difference (e.g. a ratio) between one of the 18 blood test results and a first virtual result. The first virtual result is optionally calculated by a weighted averaging of respective available results from the sample records. Optionally, each available test is weighted according to a period elapsed since the conducting thereof and the target date, optionally a date of a set of a plurality of historical test results of a target individual, referred to herein as a target date. Optionally the available tests are test taken during a first period, for example 540 days prior to the target date. For example, a weight may be calculated as an absolute value derived from time elapsed since the recording (e.g. when the test was taken) thereof. The weight may be calculated as a square function or any other function that is monotonous to the absolute value.
3. 18 features each include a difference (e.g. a ratio) between one of the 18 blood test results and a second virtual result, which is optionally calculated as the above described first virtual result, based on available tests taken during a second period, for example during 1080 days prior to the target date.
4. 1 feature—the number of sets of a plurality of historical test results the user performed during a period of year before the target date.
5. 1 feature—the number of sets of a plurality of historical test results the user performed during a period between 180*6 and 180*10 days prior to the target date.
6. 1 feature—the age of the individual, for example the individual's birth year.
7. 57 features which are squared values of all the above features (detailed in points 1-6).

Optionally, one or more biochemical blood test results may be documented per individual and optionally added as feature to the set of features. These features may be treated as the blood test results above. The biochemical blood test results may include any of the following blood test results Albumin, Calcium, Chloride, Cholesterol, Creatinine, high density lipoprotein (HDL), low density lipoprotein (LDL), Potassium, Sodium, Triglycerides, Urea, and/or Uric Acid.

Optionally, different evaluation datasets, for example matrixes, having different sets of expended features are generated to create different classifiers which classify target individuals having different demographic characteristic(s), for example gender.

Optionally, the evaluation dataset, for example the matrix, is filtered, to remove iteratively outliers. Optionally, an average deviation and/or a standard deviation of each feature is calculated and features having exceptional values, for example more than a standard deviation maximum threshold, for example 10, are truncated to the standard deviation maximum threshold. For example, the process is iteratively repeated 10 times (or less if no truncations are performed). An exemplary pseudo code that describes the cleaning process is as follows—

```
Repeat 10 times
    For each feature -
        Calculate average and standard deviation (sdv).
        For each sample -
            If (Value{sample, feature} > mean{feature}
```

```
        +10*sdv{feature})
            Value{sample, feature} = mean{feature} +9
                *sdv{feature})
        If (Value{sample, feature} < mean{feature} –
            10*sdv{feature})
            Value{sample, feature} = mean{feature} –
                9*sdv{feature}
        End samples loop
    End features loop
    Exit if no change was made
End of Repeat
```

Now, as shown at 104, the evaluation dataset is used for generating classifier(s) each classifying a gastrointestinal cancer risk of a target individual based on one or more demographic characteristics thereof and a current set of a plurality of test results, for example by the classifier generation module 205. Optionally, one or more of the following classifiers may be generated based on the evaluation dataset:

a weighted linear regression classifier where positive sample records receive a score that is about 100 times the score of negative sample records;

a K-Nearest neighbors (KNN) classifier, for example 100 times down-sampling of a negative sample record; and a random forest classifier, for example where each tree is built using a 2:1 ratio of negative to positive sample records.

Optionally, the performance of each one of the classifiers is estimated using a 10-fold cross validation process where the evaluation dataset, referred to herein as a population, is randomly split to ten equal-sized parts. For each part, the following may be performed:

selecting acceptable sets of blood test results from 90% of population not in the respective part;

training a classifier according to the selected sets of blood test results;

selecting sets of blood test results from a 10% of population in the respective part; and using the classifier on the selected sets of blood test results from the 10% of population.

Figure 3:
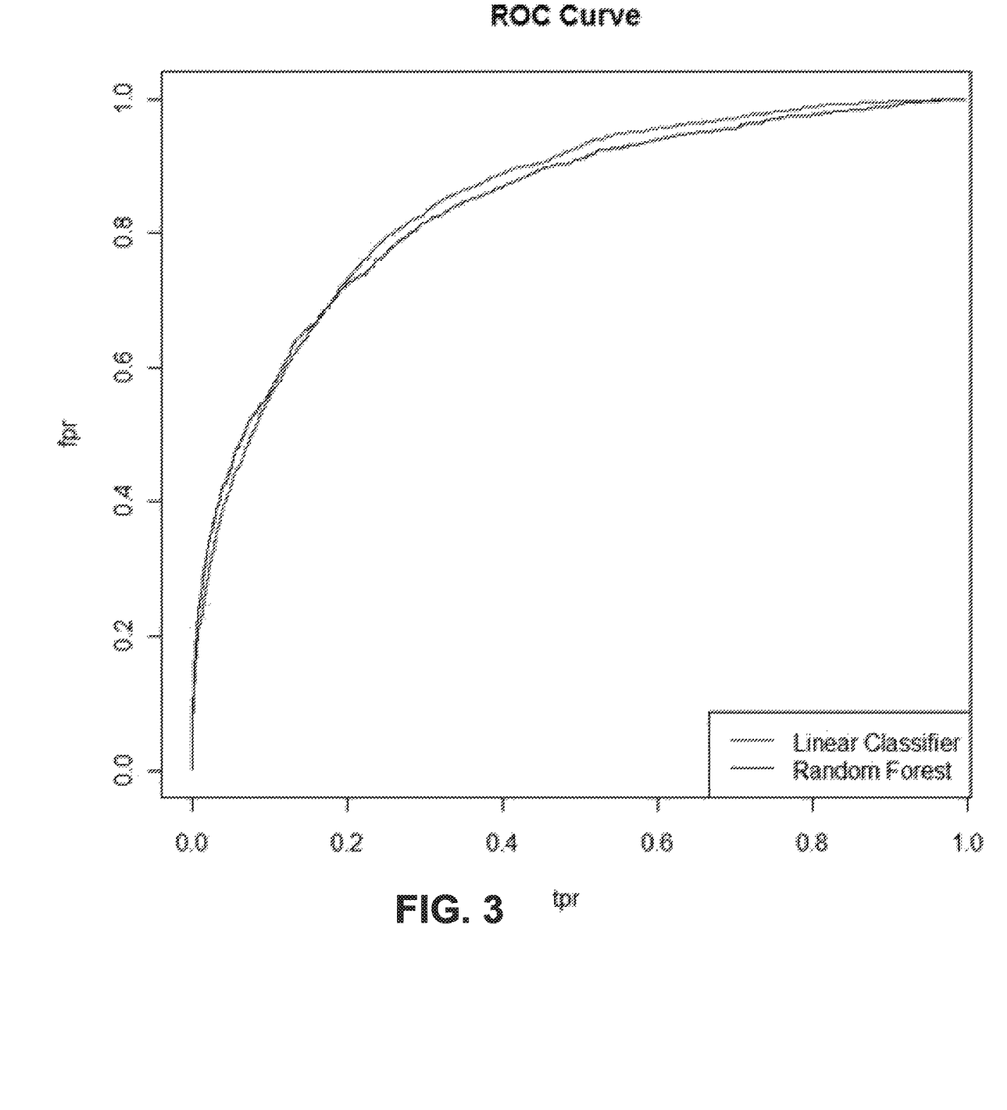
FIG. 3 is a receiving operating characteristic (ROC) curve graph, according to some embodiments of the present invention.
Figure 4A:
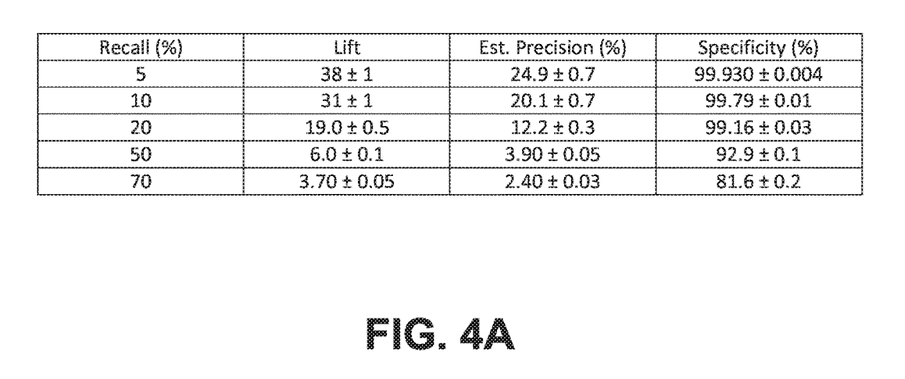
FIGS. 4A-4C are tables summarizing the performances of the different exemplary classifiers, according to some embodiments of the present invention.
Figure 4B:
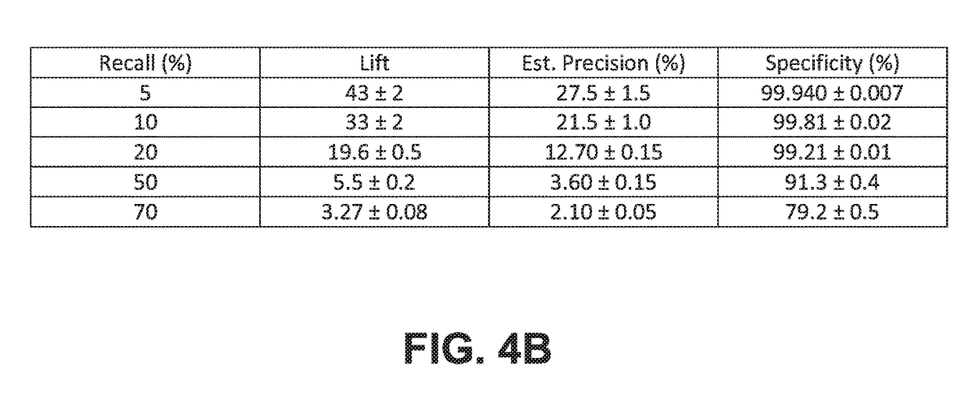
Figure 4C:
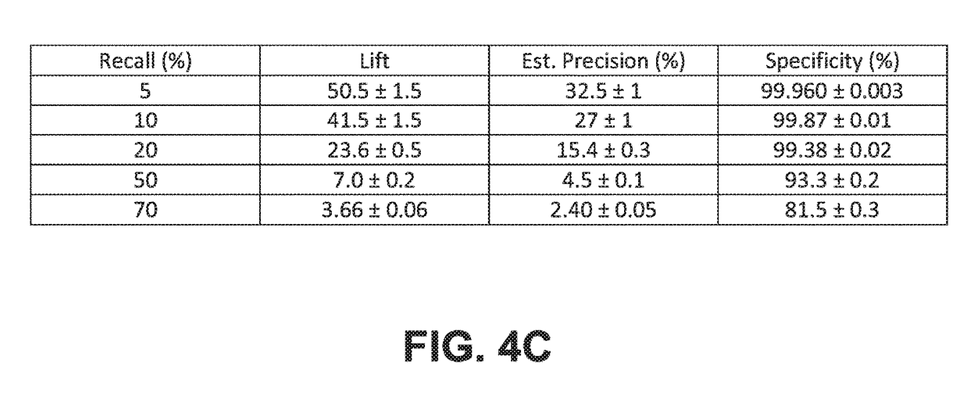

Now, classifications, also referred to as predictions, are collected to measure performance of each classifier. For example, the measures of performance are selected according to a receiving operating characteristic (ROC) curve, for example as depicted in FIG. 3. Optionally, specificity at different (5%, 10%, 20%, 50%, and 70%) sensitivity (recall) values are used for identifying the measures. The performances of the different exemplary classifiers are summarized in the tables provided in FIGS. 4A-4C which respectively have an area under curve (AUC) of 0.840±0.001, 0.820±0.001, and 0.833±0.001. It should be noted that FIG. 3 and FIGS. 4A-4C are calculated based on an overall population of 217,246 men of over 40, 1,415 have been identified as having positive colorectal cancer (CRC). Optionally, each one of the numbers in the table (Lift, Est. Precision, and Specificity) represents mean±a standard deviation (std) calculated over different cross validation schemes, for example 10.

As used herein, a recall denotes a true positive (TP) rate of TP classified individuals that equals to a percentage of CRC individuals (both TP and false negative (FN)), for example TP/(TP+FN). As used herein, precision denotes a percentage of population having classified as having CRC for example TP/(TP+FP). As used herein, a lift denotes a ratio of precision to overall CRC prevalence in the population. For example, among an overall population of 217,246 men of over 40, 1,415 have been identified as having positive CRC. In this example, the prevalence is 0.65%. The selection of negative samples to create the correct time-distribution (see above), creates a bias in the learning and testing populations, leading to CRC prevalence of 1.2%. Thus, the lift may be directly found, but only indirectly used to conclude the estimated precision by adjusting a measured precision.

Figure 5B:
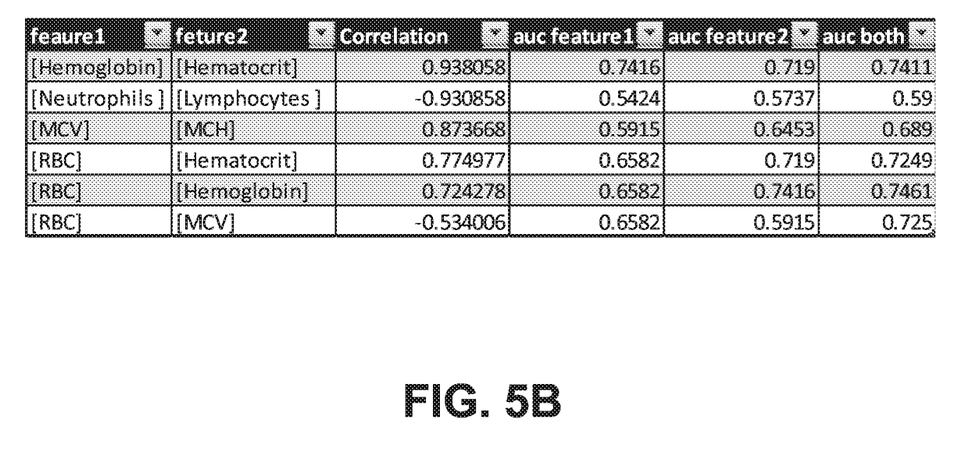
FIG. 5B is a table indicating correlation between pairs of results of blood tests.

Optionally, the set of features which are used by a certain classifier for classification are weighted according to a classification importance. The importance of a feature may be determined as an average value, over data trees, of a decrease of node impurities as measured by the Gini coefficient (statistical dispersion) due to splits. As an example, FIG. 5A depicts a table of an expended set of features which are listed according to their importance in a random forest classifier for men.

It should be noted that the historical blood test results of the classifiers and the current blood test may include pairs of blood test results of blood tests considered to be similar in nature. These pairs include one or more of the following pairs hemoglobin (HGB) and hematocrit (HCT), neutrophils percentage/count and lymphocytes percentage/count (i.e. extracted from a CBC test), MCV and MCH, RBC and hematocrit (HCT), RBC and MCV. Checking both blood results of such a pair is not trivial as for the skilled in the art these blood results have common indications and no cumulative value and therefore the skilled in the art would have use only results of one member of the pair of similar blood test and not both members of the pair of similar blood test. The inventors surprisingly found that the correlation between members of such a pair is not absolute and that the contribution to the performance of the above described classifier(s) is substantial. For example, see the table in FIG. 5B.

Figure 6:
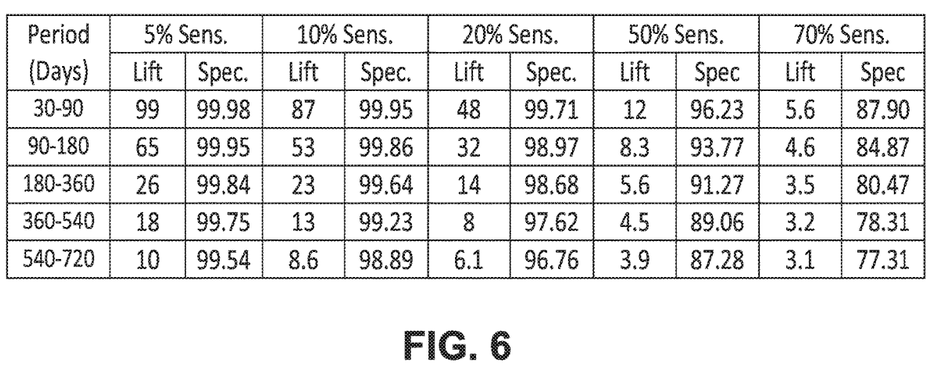
FIG. 6 is an image of a table showing performances for several time-windows.

It should be noted that the performance of a classifier depends on time between the last set of blood test results date and the cancer discovery date, for example as registered in the cancer registry. This dependency is captured by considering classifiers where acceptable blood tests for positive samples are within limited time-windows (for example 30-90 days prior to cancer registry, 90-180 days, and/or the like). For example, FIG. 6 depicts a table showing performances for several time-windows. The table shows age adjusted CBC data taken 30-720 days before diagnosis from CRC cases compared with healthy control data indicating long-term variations. In addition, for each case, the selected parameter value/result was compared to the same parameter results 1.5 years (delta 1.5) and 3 years (delta 3) prior to the selected parameter value/result evaluation. As indicated by the table of FIG. 6, the specificity is reduced when the data is older.

It should be noted that anemia in the blood, may be caused by several gastrointestinal conditions and other, with GI cancer being the least common. Unexplained anemia is a major predictor for CRC in the elderly and, together with hemorrhoids, is a common cause for delay in CRC diagnosis. Blood loss is present in 60% of CRC cases and a daily loss of as little as 3 ml in the stool can cause iron anemia. As nearly as 18% of CRC cases had anemia more than a year before diagnosis 14, however, a significant proportion are not anemic 1. Positive occult blood test may be present. However, fecal blood, the currently used for CRC screening, detects only current bleeding while in CRC, blood loss is chronic.

In Spell D W, Jones D V, Jr., Harper W F, David Bessman J. The value of a complete blood count in predicting cancer of the colon. Cancer Detect Prev 2004; 28(1):37-42 it is reported that 88% of CRC patients had at least one blood abnormality. As such, attempts to predict CRC from complete blood counts (CBC) are under active research. In a retrospective study on newly diagnosed CRC patients from which CBC parameters were available 0-122 days before diagnosis, it was shown that red blood cell distribution width (RDW) was increased above the normal range and had 84% sensitivity and 88% specificity, mainly for right sided CRC cases. No improved sensitivity in combination with RDW, hemoglobin and mean corpuscular volume (MCV) was documented.

Figure 10:
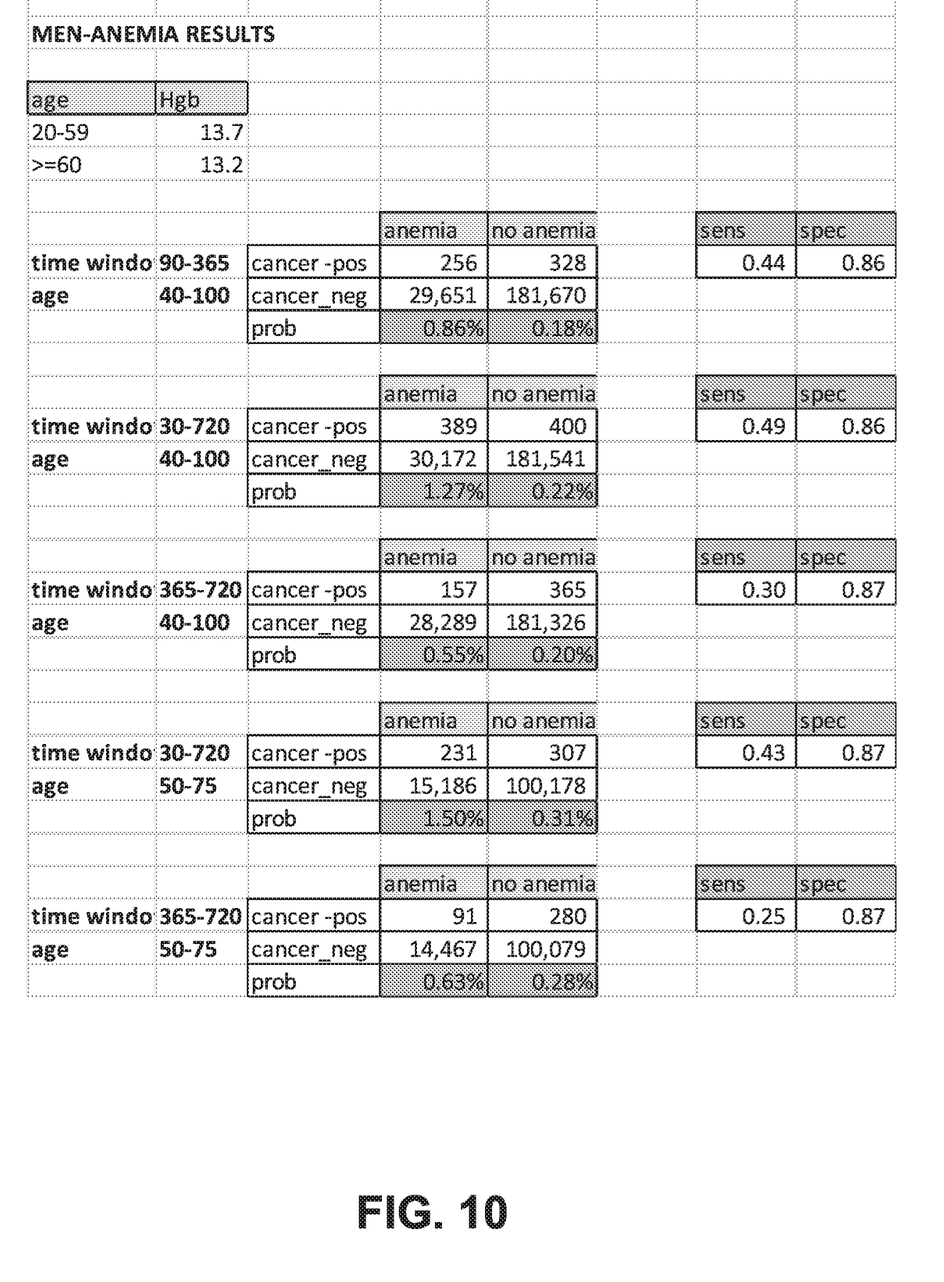
FIG. 10 is a set of tables summarizing an analysis of the results of using the above described classifiers for classifying anemic and not anemic individuals (white Americans), according to some embodiments of the present invention.

According to some embodiments of the present invention, the performance of a classifier generated as described herein may be used for classifying both individuals with anemia condition and individuals without anemia condition. For example, FIG. 10 is a set of tables summarizing an analysis of the results of using the above described classifiers for classifying anemic and not anemic individuals (white Americans). The set includes a plurality of tables, each summarizing the probability of anemic individual of a certain group of individuals in relation to non anemic individual of another group of individuals. The groups are optionally divided based on a combination between the age of the blood results and the age of the individual. FIG. 10 shows evidence that independent measures of blood counts parameters are related to CRC and that combined changes in CBC parameters, even subtle ones, within the normal range may be used as part of the CRC screening process, for example by scoring, for individual with or without anemia.

Figure 7:
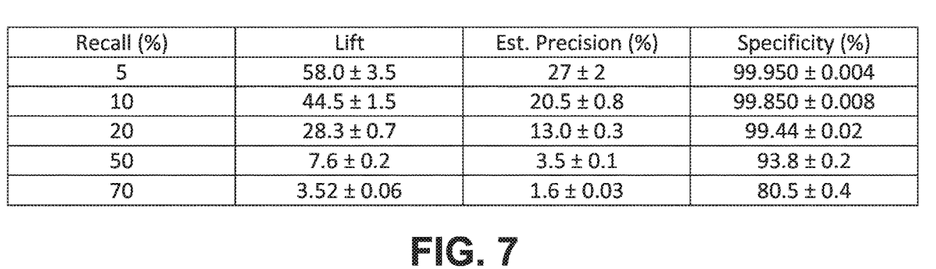
FIG. 7 is an image of a table showing performances of a Random Forest classifier.

Now, as shown at 105, the classifier(s) are outputted, optionally as a module that allows classifying target individuals, for example by the interface unit 206. Optionally, different classifiers are defined for individuals having different demographic characteristics, for example one classifier for men and another for women. For example, while a classifier that is based on a group of features from the above 18 features is set for men, a Random Forest classifier without biochemistry tests is used for women. The Random Forest classifier has an AUC of 0.833±0.001 and performances as depicted in FIG. 7 where precision is estimated according to total prevalence of 0.45%.

Figure 8:
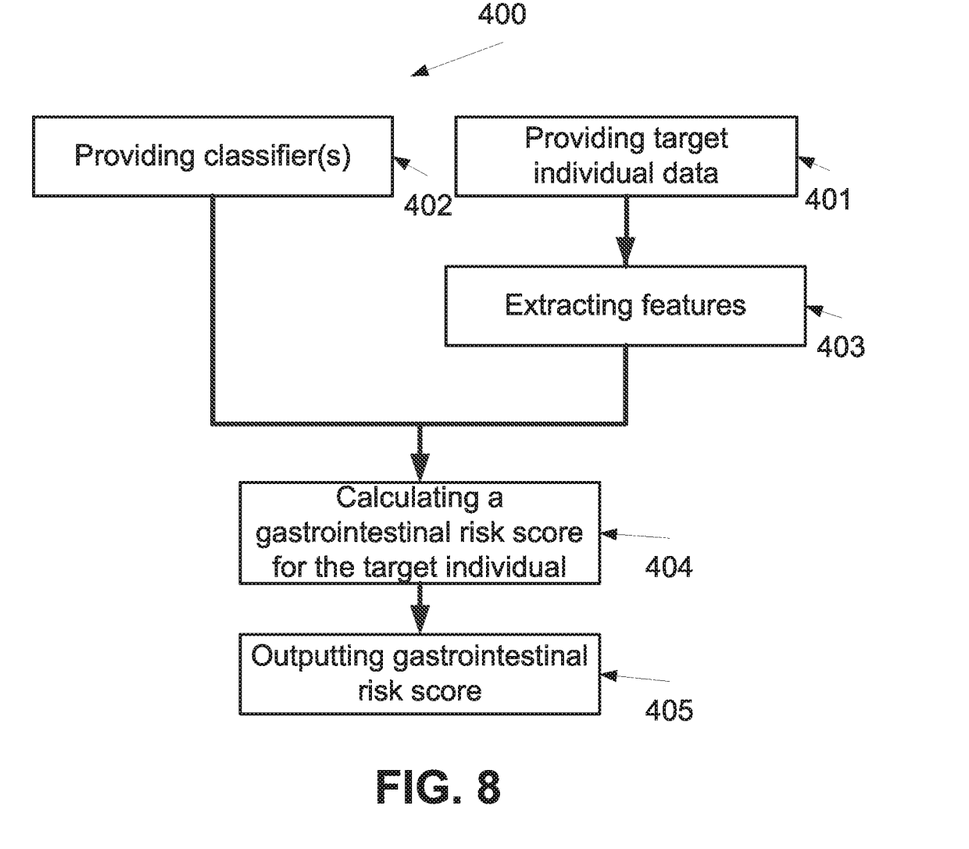
FIG. 8 is a flowchart of a method of using a classifier(s) for estimating a gastrointestinal risk score for a target individual, according to some embodiments of the present invention.

Reference is now made to FIG. 8, which is a flowchart 400 of a method of using classifier(s), such as the above classifier(s), for estimating a gastrointestinal cancer risk score for a target individual, according to some embodiments of the present invention. In use, the classifier(s) may be hosted in a web server that receives the target individual data and evaluates, using a gastrointestinal cancer evaluating module that uses the classifier(s), a gastrointestinal cancer risk score in a subject to be evaluated. The target individual data may be received via a communication network, such as the internet, from a client terminal, such as a laptop, a desktop, a Smartphone, a tablet and/or the like, which provides the set of blood test results and demographic characteristics of the subject or a reference to this target data.

First, as shown at 401 and 402, classifier(s) and a target individual data are provided. The target individual data includes one or more demographic parameter(s) and a set of a plurality of current blood test results held in the target date, which includes a number of current test results of a target individual. The target individual data may be inputted manually by a user, for example using a graphical user interface (GUI), selected by a user, optionally using the GUI, and/or provided automatically, for example by a computer aided diagnosis (CAD) module and/or system. Optionally, the target individual data includes the number of sets of blood test results the user performed during the last year, last decade and/or any intermediate period. Each one of the sets of blood test results includes blood test results, for example a group selected from the above 18 different blood test results.

Now, as shown at 403, a set of target individual features is extracted from the target individual data and optionally extended as described above.

Then, as shown at 404, the classifier(s) is used to calculate a gastrointestinal cancer risk score for the target individual by weighting each feature in the set of target individual features. Now, as shown at 405, the gastrointestinal cancer risk score is outputted.

Figure 9:
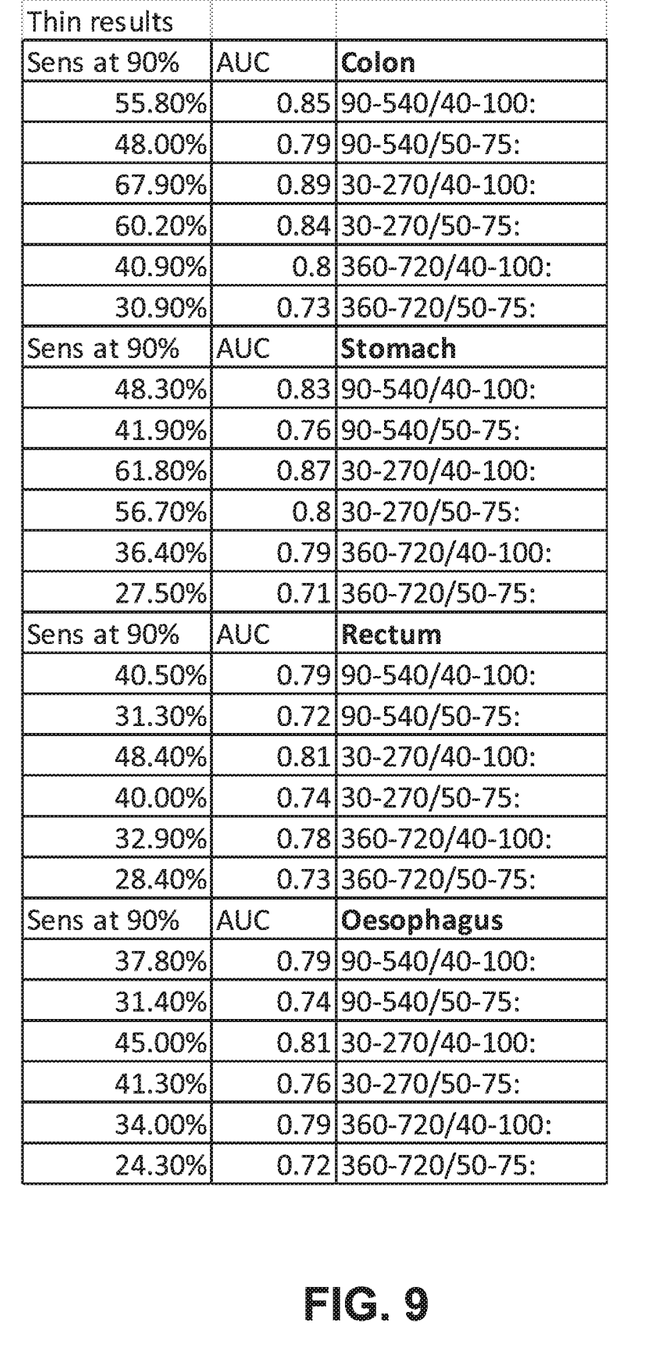
FIG. 9 is a table indicating the performances of the classifiers for each one of colon, stomach, rectum, and esophagus cancers in different sensitivities for different groups of populations, according to some embodiments of the present invention.

It should be noted that above described classifiers may be used for estimating cancer risk score for gastrointestinal cancer may be colon, stomach, rectum, or esophagus cancer. For example, FIG. 9 is a table indicating the performances of the classifiers for each one of colon, stomach, rectum, and esophagus cancers in different sensitivities for different groups of populations. Groups of populations are defined according to a combination between an age of the respective test blood results (stated in days, for instance 90-540, 90-540, 30-270, and 360-720 days, and the range of ages, for example 40-100 and 50-75. It should be noted that the table in FIG. 9 indicating the performances of the classifiers on a different population than used for the classifiers documented with reference to FIGS. 4A and 4B. In FIG. 9, the data includes results of blood tests from a total of 81,641 English individuals over the age of 40 of which 3,099 were diagnosed with colon cancer, 1,286 with rectal cancer, 578 with gastric cancer and 1,061 with esophagus cancer.

It is expected that during the life of a patent maturing from this application many relevant systems and methods will be developed and the scope of the term a processor, a display, and user interface is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computerized method for providing a client terminal with an increased accuracy evaluation of gastrointestinal cancer risk, with no highly invasive examination, in response to an indication of current blood test results of a patient, comprising:
   receiving by a computing system associated with a database storing a plurality of classifiers and from a client terminal and via a network, an indication of values of a plurality of current blood test results calculated based on an analysis of a blood collected from a target individual;
   calculating an increased accuracy evaluation of a gastrointestinal cancer risk of said target individual without using highly invasive examination, by:
      generating, by said computing system, a combination of at least 10 blood test features based on said plurality of current blood test results, each one of said at least 10 different blood test features is based on a blood test value of one of said plurality of current blood test results;
      selecting at least one classifier according to at least one demographic characteristic of said target individual from said plurality of classifiers, each of said plurality of classifiers is generated according to a plurality of respective historical blood test results of a plurality of sampled individuals having at least one different demographic characteristic, said at least one classifier is generated according to an analysis of said plurality of respective historical blood test results of each of another of said plurality of sampled individuals; and
      evaluating, using a hardware processor of said computing system, a gastrointestinal cancer risk of said target individual by classifying said combination of at least 10 different blood test features using said at least one classifier; and
   outputting said gastrointestinal cancer risk for presentation by said client terminal;
   wherein each of said plurality of historical and current blood test results comprises results of at least one the following blood tests: white blood cell count— WBC (CBC); mean platelet volume (MPV); mean cell; platelet count (CBC); eosinophils count; neutrophils percentage; monocytes percentage; eosinophils percentage; basophils percentage; and neutrophils count; and monocytes count;
   wherein said at least one classifier is generated according to each of said plurality of historical test results that individually have insufficient statistical significance correlating between said respective test result and having gastrointestinal cancer.

2. The method of claim 1, wherein said gastrointestinal cancer risk is for a cancer selected from a group consisting of colon cancer, stomach cancer, rectum cancer, and esophagus cancer.

3. The method of claim 1, wherein said at least one classifier is generated according to an analysis of an age of each of said plurality of sampled individuals.

4. The method of claim 1, wherein each of said plurality of historical and current blood test results comprises results of Platelets hematocrit (PCT).

5. The method of claim 1, wherein said at least one classifier comprises a member of a group consisting of: a weighted linear regression classifier, a K-Nearest neighbors (KNN) classifier, and a random forest classifier.

6. The method of claim 1, wherein said at least one classifier is generated according to an analysis of at least one demographic characteristic of each of said plurality of sampled individuals.

7. The method of claim 1, wherein each of said plurality of historical and combination of at least 10 current blood test results comprises results of Platelets hematocrit (PCT).

8. A system for providing a client terminal with an increased accuracy evaluation of gastrointestinal cancer risk, with no highly invasive examination, in response to an indication of current blood test results of a patient, comprising:
   a database storing a plurality of classifiers;
   an interface adapted for receiving from a client terminal, via a network, an indication of values of a plurality of current blood test results calculated based on an analysis of a blood collected from a target individual;

a memory storing code; and a hardware processor coupled to the interface, the database, and the memory for executing the stored code, the code comprising:

instructions for calculating an increased accuracy evaluation of a gastrointestinal cancer risk of said target individual without using highly invasive examination, by:

generating a combination of at least 10 blood test features based on said plurality of current blood test results, each one of said at least 10 different blood test features is based on a blood test value of one of said plurality of current blood test results;

selecting at least one classifier according to at least one demographic characteristic of said target individual from said plurality of classifiers, each of said plurality of classifiers is generated according to a plurality of respective historical blood test results of a plurality of sampled individuals having at least one different demographic characteristic, said at least one classifier is generated according to an analysis of said plurality of respective historical blood test results of each of another of said plurality of sampled individuals; and evaluating a gastrointestinal cancer risk of said target individual by classifying said combination of at least 10 different blood test features using said at least one classifier; and instructions for outputting said gastrointestinal cancer risk for presentation by said client terminal;

wherein each of said plurality of historical and current blood test results comprises results of at least one the following blood tests: white blood cell count— WBC (CBC); mean platelet volume (MPV); mean cell; platelet count (CBC); eosinophils count; neutrophils percentage; monocytes percentage; eosinophils percentage; basophils percentage; and neutrophils count; and monocytes count;

wherein said at least one classifier is generated according to each of said plurality of historical test results that individually have insufficient statistical significance correlating between said respective test result and having gastrointestinal cancer.

9. The system of claim 8, wherein said gastrointestinal cancer risk is for a cancer selected from a group consisting of colon cancer, stomach cancer, rectum cancer, and esophagus cancer.

10. The system of claim 8, wherein said at least one classifier is generated according to an analysis of an age of each of said plurality of sampled individuals.

11. The system of claim 8, wherein each of said plurality of historical and current blood test results comprises results of Platelets hematocrit (PCT).

12. The system of claim 8, wherein said at least one classifier comprises a member of a group consisting of: a weighted linear regression classifier, a K-Nearest neighbors (KNN) classifier, and a random forest classifier.

13. The system of claim 8, wherein said at least one classifier is generated according to an analysis of at least one demographic characteristic of each of said plurality of sampled individuals.

14. The system of claim 8, wherein each of said plurality of historical and combination of at least 10 current blood test results comprises results of Platelets hematocrit (PCT).

15. A computer program product comprising a non-transitory computer readable storage medium storing program code thereon for implementation by at least one processor, for providing a client terminal with an increased accuracy evaluation of gastrointestinal cancer risk, with no highly invasive examination, in response to an indication of current blood test results of a patient, comprising:

instructions for receiving by a computing system associated with a database storing a plurality of classifiers and from a client terminal and via a network, an indication of values of a plurality of current blood test results calculated based on an analysis of a blood collected from a target individual;

instructions for calculating, by said computing system, an increased accuracy evaluation of a gastrointestinal cancer risk of said target individual without using highly invasive examination, by:

generating a combination of at least 10 blood test features based on said plurality of current blood test results, each one of said at least 10 different blood test features is based on a blood test value of one of said plurality of current blood test results;

selecting at least one classifier according to at least one demographic characteristic of said target individual from said plurality of classifiers, each of said plurality of classifiers is generated according to a plurality of respective historical blood test results of a plurality of sampled individuals having at least one different demographic characteristic, said at least one classifier is generated according to an analysis of said plurality of respective historical blood test results of each of another of said plurality of sampled individuals; and instructions for evaluating, using a hardware processor of said computing system, a gastrointestinal cancer risk of said target individual by classifying said combination of at least 10 different blood test features using said at least one classifier; and instructions for outputting said gastrointestinal cancer risk for presentation by said client terminal;

wherein each of said plurality of historical and current blood test results comprises results of at least one the following blood tests: white blood cell count— WBC (CBC); mean platelet volume (MPV); mean cell; platelet count (CBC); eosinophils count; neutrophils percentage; monocytes percentage; eosinophils percentage; basophils percentage; and neutrophils count; and monocytes count;

wherein said at least one classifier is generated according to each of said plurality of historical test results that individually have insufficient statistical significance correlating between said respective test result and having gastrointestinal cancer.

* * * * *